United States Patent [19]

Venkateswaran et al.

[11] Patent Number: 4,673,575
[45] Date of Patent: Jun. 16, 1987

[54] COMPOSITION, PHARMACEUTICAL PREPARATION AND METHOD FOR TREATING VIRAL HEPATITUS

[75] Inventors: Pinayur S. Venkateswaran, Chester; Irving Millman, Willow Grove; Baruch S. Blumberg, Philadelphia, all of Pa.

[73] Assignee: Fox Chase Cancer Center, Philadelphia, Pa.

[21] Appl. No.: 727,452

[22] Filed: Apr. 26, 1985

[51] Int. Cl.$^4$ ............................................. A61K 35/78
[52] U.S. Cl. .................................................. 424/195.1
[58] Field of Search ...................................... 424/195.1

[56] References Cited

PUBLICATIONS

Thyagarjan et al., Indian J. Med. Res. 76, (Suppl.; Dec. 1982), pp. 124–130.
Dhar et al., Indian J. Exp. Biol. 6 (1986), pp. 232-247.
Bhargava et al., Indian J. Chem., 8 (1970), pp. 664–665.
Mahra et al., Indian J. Pharm. 30 (1968), p. 284.
Steinmetz, Codex Vegetabilis, 1957, No. 828.
Gellis et al., Current Ped. Therapy, 1982, p. 202.
Cecil, A Textbook of Medicine, 1955, p. 922.

*Primary Examiner*—Johnnie R. Brown
*Assistant Examiner*—John W. Rollins, Jr.
*Attorney, Agent, or Firm*—Dann, Dorfman, Herrell & Skillman

[57] ABSTRACT

A pharmaceutical preparation comprising the methanol extractable components of *Phyllanthus niruri* L. is administered to patients suffering from hepatitis B virus infection in an amount effective for inhibiting the growth of said virus.

11 Claims, 4 Drawing Figures

COMPOSITION, PHARMACEUTICAL PREPARATION AND METHOD FOR TREATING VIRAL HEPATITUS

The present invention relates to a composition of matter, derived from *Phyllanthus niruri* L., to a pharmaceutical preparation containing the composition of matter, and to the use of the pharmaceutical preparation in the treatment of chronic hepatitis virus infection.

*Phyllanthus niruri* Linn is a perennial herb common to central and southern India that has been used in folk medicines to treat a variety of maladies. For example, in Volume 1, "Doctor K. M. Nadkarni's Indian Matrial Medica" (3rd Ed.; revised and enlarged by A. K. Nadkarni, p. 948), it is stated that the plant is considered de-obstruent, diuretic, astringent and cooling and formulations for the treatment of jaundice, as well as some forms of dropsy, gonorrhoea, menorrhagia and other genitourinary affections of a similar type are described. It is further stated that the juice of the stem may be mixed with oil for use in opthalmia and that the whole plant may be pounded with its root and combined with rice water to provide a poultice for ulcers, sores and swellings. A poultice of the leaves mixed with salt is purported to cure itch and other skin affections. A bitter neutral substance named "phyllanthin" has been isolated from the plant. As a stomachic bitter, it is said to be useful in dyspepsia. The plant is also said to be useful in treating diabetes.

Insofar as is known, however, *Phyllantus niruri* Linn has not been proposed heretofore for the treatment of viral hepatitis infection.

Viral hepatitis is a known cause of chronic liver disease. Studies have established a link between certain types of viral hepatitis, including hepatitis B virus, (HBV) and primary hepatocellular carcinoma and liver failure.

A significant breakthrough against viral hepatitis came with the discovery of Australia antigen in the serum of Australian aborigines. Blumberg, Bull. N.Y. Acad. Med. 40, 377 (1964). A vaccine consisting of Australian antigen has been proven effective in preventing the spread of viral hepatitis infection. See U.S. Pat. No. 3,636,191. However, the vaccine does not direct treatment against the carrier state. The persistence of hepatitis virus in the carrier state remains cause for concern, due to the continuing risk of spread of infection to those who have not been vaccinated. In addition, carriers themselves are in danger of developing primary hepatocellular carcinoma.

Treatments previously attempted on patients diagnosed as having chronic hepatitis viral infection have been varied and generally ineffective. In Volume 29, *Advances in Internal Medicine*, "Therapy for Chronic Active Hepatitis" by L. B. Seeff et al., pp. 109-145 (1984), there is reported a number of anti-viral drugs that have been investigated for use in drug therapy against viral-releated chronic active hepatitis. The authors acknowledge that much interest is evoked by the new experimental forms of treatment, but none has proved to be consistently effective, and for some, toxicity is high. The authors further state that all of the experimental forms of treatment appear to reduce levels of replicating virus, in vitro but none clearly affects HBsAg or disease activity in vivo.

Immunotherapy involving the infusion of anti-HBsAg in patients afflicted with persistent HBV infection has failed to alter the course of the infection.

Thus, no clearly effective therapy is currently available for patients having chronic hepatitis virus infection, which patients represent the bulk of cases in the United States.

SUMMARY OF THE INVENTION

In accordance with one aspect of the present invention, there is provided a composition of matter useful in the treatment of hepatitis B virus infection which consists essentially of the methanol-extractable component of *Phyllanthus niruri* L.

As used herein, the expression "methanol extractable component of *Phyllanthus niruri* L." includes methanol extracts from the whole or any part of the plant, obtained either directly, (in a one-step extraction), or in a fractional extraction using additional solvents, such as water, benzene and/or hexane.

In accordance with another aspect of the present invention, there is provided a pharmaceutical preparation for the treatment of hepatitis B virus infection which comprises, as the active agent, the aforesaid composition in an amount effective to inhibit growth of the hepatitis virus.

In accordance with a further aspect of the present invention, there is provided a method for treating patients suffering from hepatitis virus infection, which comprises administering to said patients the above described pharmaceutical preparation.

It has been discovered in accordance with the present invention that a component extractable from *Phyllanthus niruri* L. exhibits significant hepatitis B virus inhibitory activity in vivo and shows no evidence of toxicity to mammalian cells. Since the chemical nature of the component of *Phyllanthus niruri* L. responsible for the observed hepatitis B virus inhibitory activity has not been clearly defined, it may be a single chemical or a mixture of substances. Accordingly, the singular of the term 'component', as used herein, also includes the plural.

Among the significant properties of this substance is that it inhibits DNA polymerase of HBV and binds to HBsAg, in vitro. The fact that both HBV-DNA polymerase inhibitory activity and HBsAg binding activity are possessed by an insolable component of *Phyllanthus nirui*, L. may be important. Substances which have been proposed heretofore for drug therapy against chronic hepatitis B virus infection based on evidence of HBV-DNA polymerase inhibitory activity in vitro alone, such as phosphonoformate, have been found to be ineffective in controlling the disease e.g. in infected chimpanzees.

Hepatitis B virus, which afflicts humans, has been shown to be very similar to woodchuck hepatitis virus (WHV), which infects woodchucks. Woodchucks infected with WHV may show acute and chronic hepatitis and some woodchucks with chronic hepatitis may develop primary hepatocellular carcinoma. This pattern is very similar to what is found in humans infected with HBV. The molecular biology of HBV and WHV are also very similar. See, for example, O. Hantz et. al., Vol. 25 (No. 2) Antimicrobial Agents and Chemotherapy pp. 242-246, February 1984; I. Millman et. al., Vol. 4 (No. 5) Hepatology pp. 817-824, 1984; and references cited therein.

DETAILED DESCRIPTION OF THE INVENTION

The discovery that *Phyllanthus niruri* L. contains active component useful in the treatment of hepatitis virus infection resulted, in part, from tests in vitro for biological activity showing that a component of the plant material possesses binding activity with HBsAg and the ability to inhibit HBV-DNA polymerase. These tests were followed by in vivo studies in which an aueous extract of *Phyllanthus niruri* L. was administered to a number of woodchucks infected with woodchuck hepatitis virus (WHV). After a period of approximately four to six weeks, a majority of the treated woodchucks were found to be WHV negative. As a result of these promising in vivo studies, a systematic analysis of *Phyllanthus niruri* L. was undertaken to isolate and purify the active agent responsible for the hepatitis virus inhibiting activity.

HBV-DNA polymerase inhibitory activity and HBsAg binding activity were determined using an aqueous extract of the whole plant, i.e. stem, leaves and roots.

Figure 1:
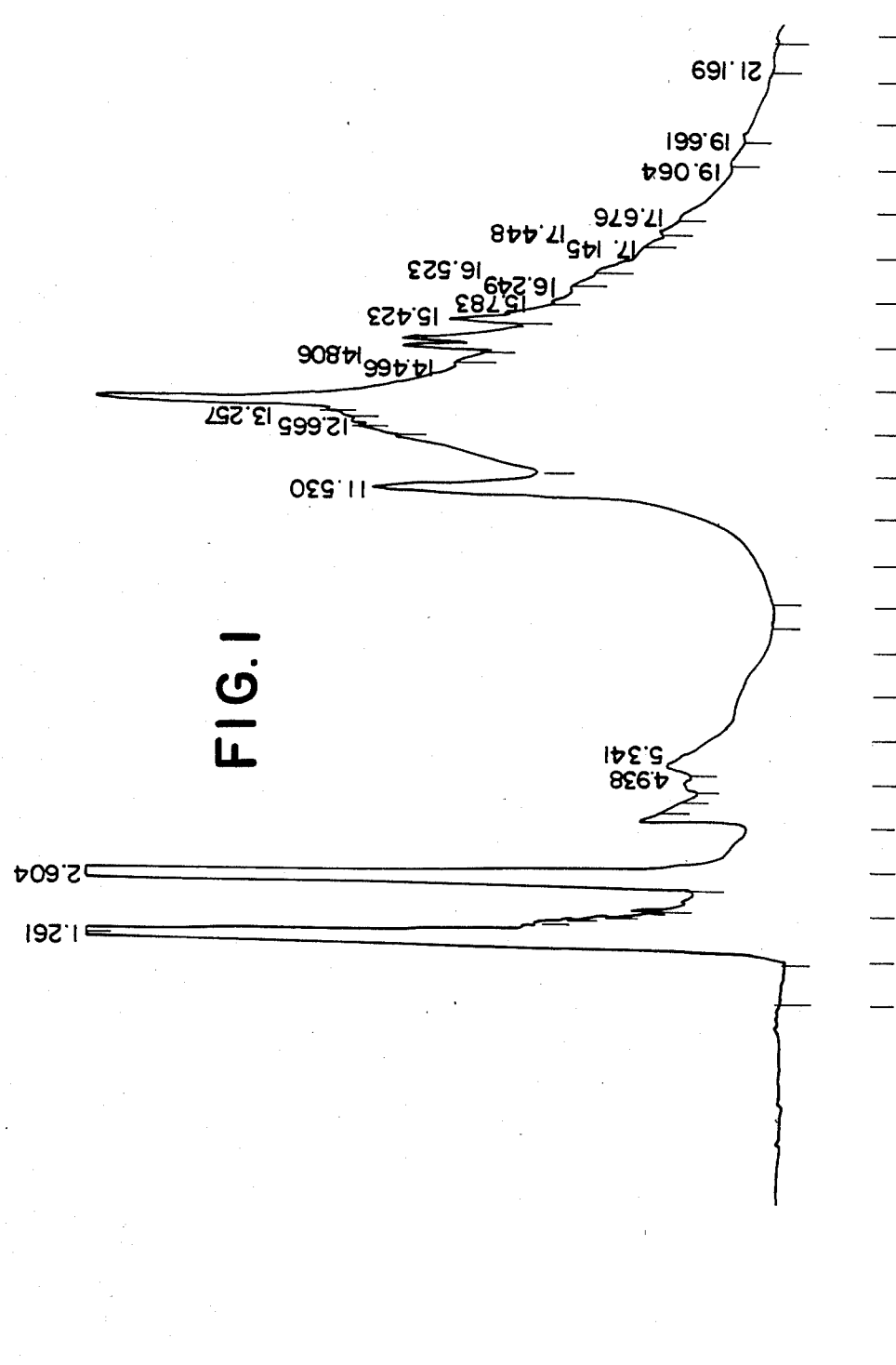

FIG. 1 represents the elution profile of HPLC on C-18 reverse phase column using a solvent system of 1% acetic acid: acetonitrile at a ratio of 60:40. The procedures employed in testing the aqueous extract of *Phyllanthus niruri*, L. for HBV-DNA polymerase inhibitory activity and HBsAg binding activity, are described in detail hereinbelow.

Figure 2:
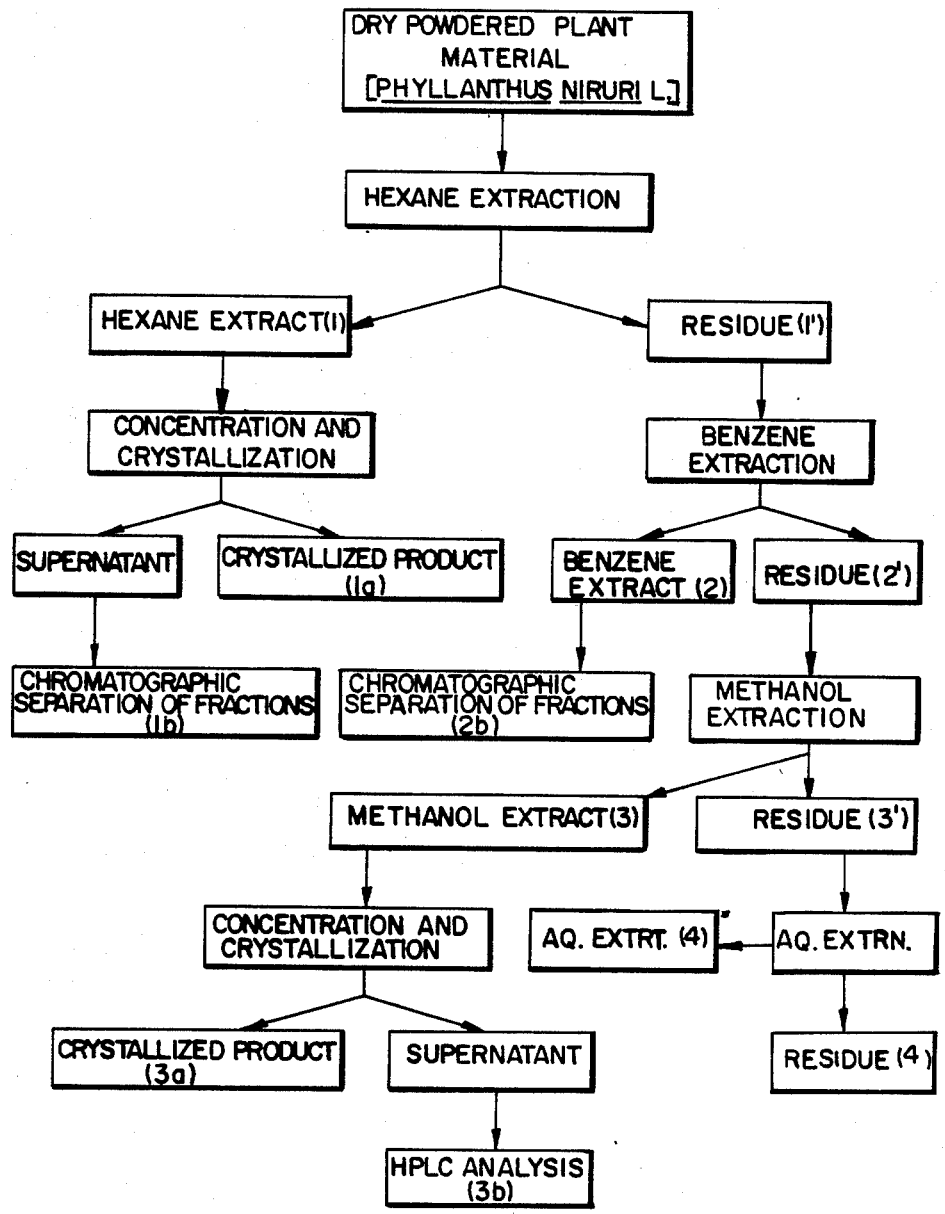

The component having hepatitis virus-inhibitory activity may be derived from *Phyllanthus niruri* L. by fractional extraction. A suitable procedure for the isolation of the active component is ilustrated in FIG. 2. Dried, powdered, plant material, preferably from the whole plant, is extracted with hexane, and hexane extract (1) and residue (1') are separated. The hexane extract is concentrated to promote crystallization of crystallizable components and the crystallized product (1a) is separated from the supernatant. The soluble fractions (1b) in the supernatant are separated chromatographically. The residue of the hexane extract undergoes extraction with benzene and the benzene extract (2) and residue (2') are separated. The soluble fractions (2b) of the benzene extract are separated chromatographically. The benzene residue is further extracted with methanol and the methanol extract (3) is separated from the residue (3'). The methanol extract is processed in the same general manner as the hexane extract, described above, and results in crystallized product (3a) and fractions (3b), which later are chomatographically separated from the supernatant. The residue of the methanol extraction is subjected to aqueous extraction and the aqueous extract (4') is separated.

The benzene and methanol extracts were found to have significant HBsAg binding activity and the latter exhibited HBV-DNA polymerase inhibiting activity, as well. By contrast, the aqueous extract of the residue of hexane, benzene and methanol extractions had limited HBsAg binding activity, but possessed considerable HBV-DNA polymerase inhibiting activity. Fractions 2b and 3b obtained from the benzene extract and methanol extract, respectively, both exhibited significant HBsAg binding activity and fraction 3b had, in addition, HBV-DNA polymerase inhibiting activity, as did the crystallized produce 3a of the methanol extraction, except that the HBV-DNA polymerase inhibiting activity of the latter was less pronounced. The relative degree of HBsAg binding activity and HBV-DNA polymerase inhibiting activity for each of the aforementioned *Phyllanthus niruri* L. fractions was determined and is set forth, along with its physical state, in Table I, below.

TABLE I

| Fraction No. | Fraction | Physical State | HBV-DNA polymerase inhibition assay | HBsAg binding activity assay |
|---|---|---|---|---|
| 1 | Hexane extract | syrup | Neg. | a |
| 1a | Hexane extract crystals | white solid crystalline (IR, NMR spectra) | Neg. | a |
| 1b | Hexane extract supernatant fluid (Further fractionated on silica gel column) | liquid | a | a |
| 2 | Benzene extract | liquid | a | 93-95%[b] |
| 2b | Benzene extract fractionated on silica gel column | liquid | Not performed | 87% |
| 3 | Methanol extract | syrup | Pos. (++) | 87% |
| 3a | Methanol extract crystals | brown solid (NMR spectrum) | Pos. (+) | 92% |
| 3b | Methanol supernatant fluid | liquid | Pos. (++) | 94% |
| 4 | Aqueous extract of the residue of hexane, benzene and methanol extraction | red-brown solution | Pos. (++++) | 12% |

Figure 3:
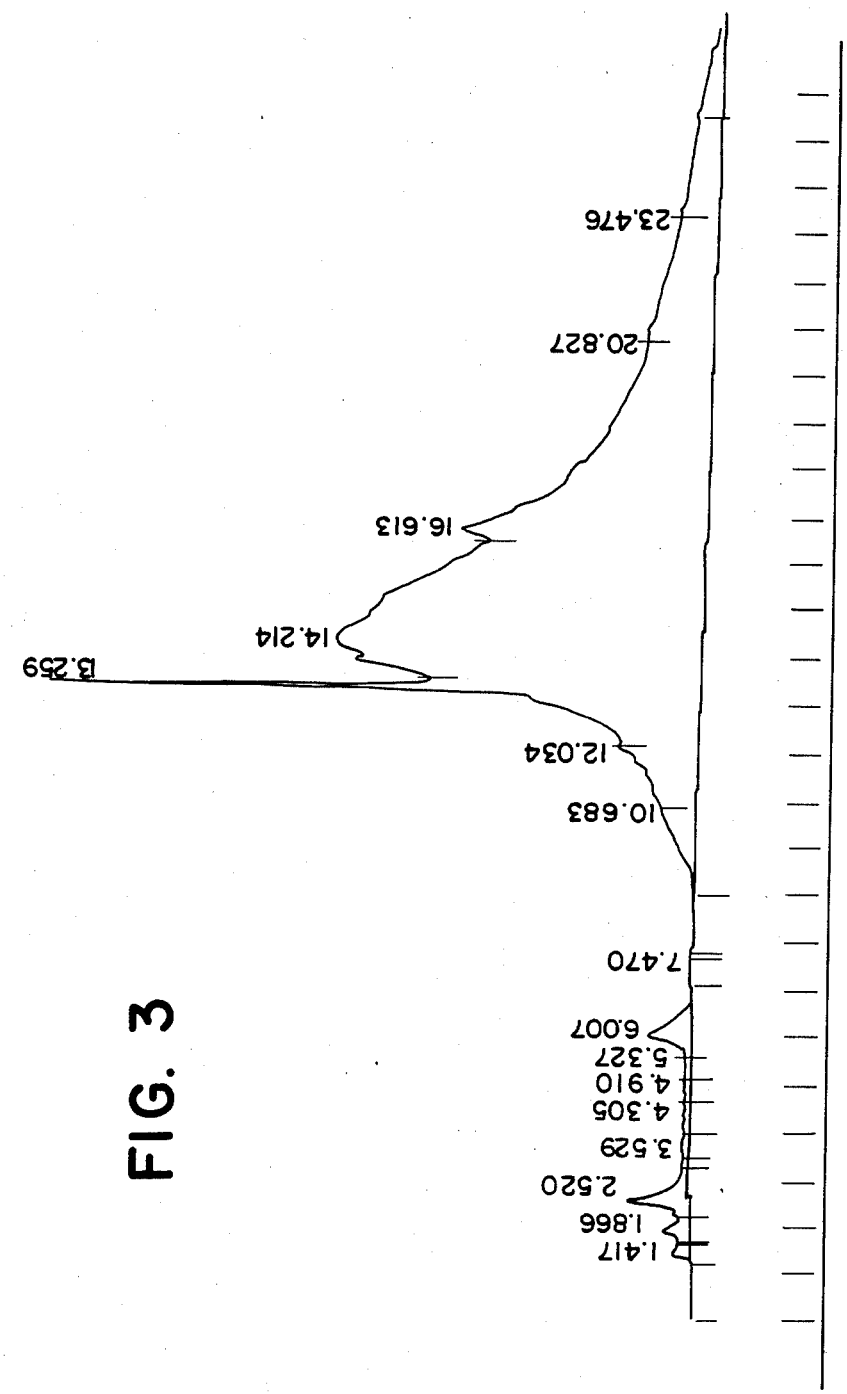

[a] Insoluble in aqueous media in which DNA polymerase assay and HBsAG binding activity were performed.
[b] In aqueous ethylene glycol for solubilization FIG. 3 represents the elution profile of HPLC, under conditions identical to those used on the aqueous extract in FIG. 1, of the methanol extract (fraction 3b) obtained from the fractional extraction. As can be seen from comparing FIG. 1 with FIG. 3, of the three major peaks appearing in FIG. 1, FIG. 3 contains only the peak eluting between 12 and 20.8 minutes. The first two peaks have apparently been eliminated by the previous extractions with organic solvents, hexane and benzene.

Based on the data presented in FIGS. 1 and 3 and Table I, it is believed that the major inhibitory activity of *Phyllanthus niruri* L. is present in the methanol extract. As shown in Table I, the methanol extract exhibits significant HBV-DNA polymerase inhibitory activity and HBV binding activity.

The replication of hepatitis B virus can be prevented when one or more of the following functions are inhibited: (i) HBV-DNA polymerase; (ii) entry of virus into liver cells. The former can be achieved by inhibiting the enzyme HBV polymerase; and the latter by binding to the hepatitis surface antigen various reagents, including anti-HBsAg. The aqueous extract of *Phyllanthus niruri* L. apparently contains both of the aforementioned activities and for that reason was used in in vivo studies on woodchuck carriers of WHV. These studies are described in detail hereinbelow.

The pharmaceutical preparation of the present invention may be administered using any amount and method effective for inhibiting growth of hepatitis virus. The active component of *Phyllanthus niruri* L. used in the practice of the present invention has been shown to have no detectable toxicity as determined by the NIH standard mouse toxicity test recommended by the FDA for pertussis vaccine. This test is also described in detail hereinbelow.

The pharmaceutical preparation is conveniently administered in dosage unit form from about 400 micrograms to about 100 milligrams/kilogram of body weight, with a range of about 1 to about 20 milligrams/kilogram of body weight being preferred.

The pharmaceutical preparation may include a biologically acceptable medium suited to the particular mode of administration. For example, a suitable biological buffer, such as phosphate buffered saline pH 7.4 (PBS) may be used in parenteral administration.

The preferred route for administering the pharmaceutical preparation is intraveneous or intraperitoneal in the form of a dosage unit. Other modes of administration may also be effective, such as oral or subcutaneous administration.

The pharmaceutical preparation may be administered at appropriate intervals, e.g., once or twice a week, until serum markers of the hepatitis virus (e.g. HBsAg and viral endogenous DNA polymerase) dissappear. The appropriate interval in a particular case will normally depend on the condition of the patient. As used herein, the term "patient" includes both humans and animals.

Of course the methanol must be removed from the active component before administration to a patient. This may be conveniently done by evaporating the methanol in vacuo and redissolving the methanol-free dry residue in biological medium, e.g. PBS.

The following examples are provided for further understanding of the present invention.

EXAMPLE 1

This example describes the preparation of an aqueous extract of *Phyllanthus niruri* L. and the testing of same to determine HBsAg binding activity and HBV-DNA polymerase inhibitory activity.

(a) Preparation of extract. Whole plants of *Phyllanthus niruri* L. were dried and powdered. Forty g of the powdered material was extracted with 200 ml of distilled water at 60° C. for 4 hours. The extract which was red-brown in color, was filtered and the filtrate was centrifuged at 10,000 rpm for 20 minutes at 25° C. The supernatant was sterilized by filtering through 0.45 u millipore filter. The sterilized extract was stored in aliquots of 3 ml in sterile vials.

In order to estimate the weight of the soluble materials, one milliliter of the extract was lyophilized in a pre-weighed vial, and the vial was weighed again with the lyophilized extract. The concentration of the extract was found to be 18 mg/ml.

(b) In vitro tests of effect of plant extract on hepatitis B virus surface antigen. The above extract was diluted 2-, 4- and 8-fold and was added to equal volume of serum containing HBsAg. Then the mixture was assayed for HBsAg by a routine procedure using Ausria II assay kit (Abbott Laboratories). The extract gives 95–97% inhibition of binding of HBsAg with antibody to HBsAg by this method at concentrations of 4 and 2 mg/ml and about 75% at 1 mg/ml, indicating interference in the binding of HBsAg to the antibody against it.

(c) Inhibition of endogenous HBV-DNA polymerase. Aqueous extracts of *Phyllanthus niruri* L., at a concentration of 4, 2 and 1 mg/ml, were added to HBV particles centrifuged from HBV-positive sera. Then nucleotide triphosphates ATP, GTP, CTP and 32p-TTP were added in the presence of 0.05M Tris HCl, pH 8.0, containing 10 uM $MgCl_2$, 0.15M NaCl, 1 mM DTT and 0.1% NP40. After 2 hours at 37° C., the reaction was stopped by addition of pronase (0.5 mg/ml) in 0.1% SDS containing 0.01M EDTA in Tris HCl, pH 7.4. The reaction mixture was subjected to electrophoresis on 1.5% agarose, using bromophenol blue as tracking dye. The gel slab was then dried on a filter paper for autoradiography.

Figure 4:
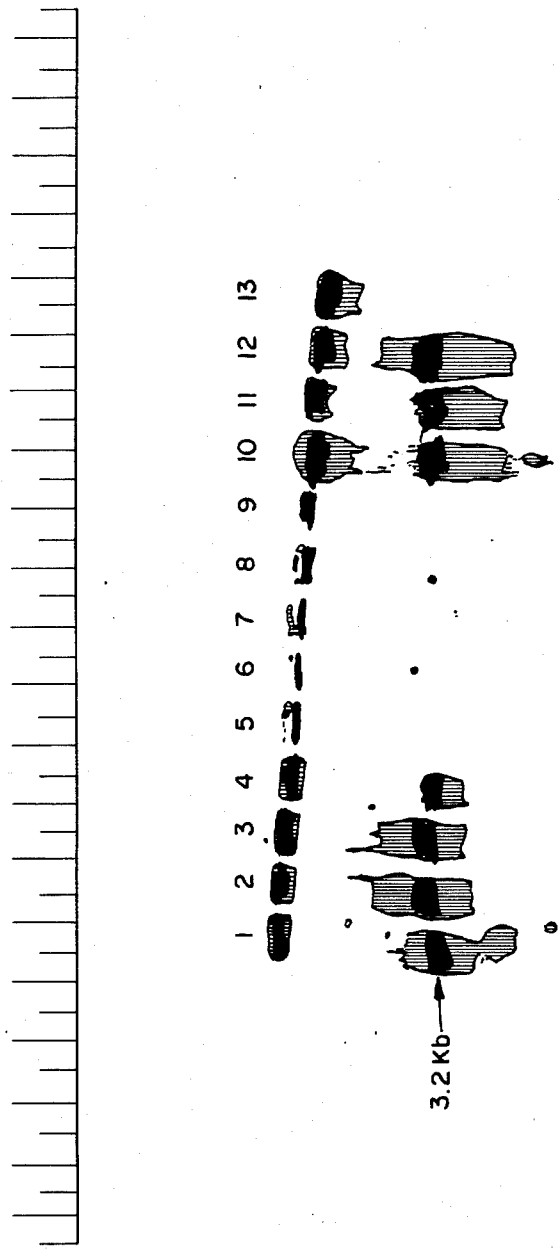

The result of the autoradiography (which is reproduced in FIG. 4) shows that the aqueous extract at all three concentrations inhibits the endogenous HBV-DNA polymerase as indicated by the absence in Lanes 5, 6, 7, 8 and 9 of a band at 3.2 kb area, indicated by the arrow.

The assays employed in this example were the same as those referred to in Table I above.

EXAMPLE 2

This example, described in vivo studies of the effect of *Phyllanthus niruri* L. extract on woodchucks infected with woodchuck hepatitis virus.

Seven woodchucks infected with WHV were used in these studies. An aqueous extract of *Phyllanthus niruri* L. (at a concentration of 9 mg/0.5 ml of soluble matter), was administered to four of the woodchucks twice a week, while the other three received sterile phosphate buffered saline (PBS), pH 7.2 in 0.5 ml. doses, twice a week. The course of the infection was followed by assay for the presence of woodchuck hepatitis surface antigen (WHsAg) titre as well as the presence of DNA polymerase activity in the WHV particles in the sera of these animals, starting one week before the start of the treatment and then by weekly bleedings. Three of the four animals treated with *Phyllanthus niruri* extract showed a drop in WHsAg titre 21 days after the start of the drug and showed no detectable antigen between 28 and 36 days and remained so until the 77th day, at which time treatment with the aqueous extract of *Phyllanthus niruri* L. was discontinued. WHV-DNA polymerase activity in these animals followed a similar trend, although the polymerase enzyme activity lagged 7 to 14 days before becoming negative. The fourth animal did not respond to the treatment and it died on the 56th day because of infections unrelated to WHV.

Of the three control animals, one died on the 64th day. The other two showed a steady titre of WHsAg and DNA polymerase activity until the 77th day, when the administration of PBS was stopped.

After 154 days, the three treated aninmals that responded to the treatment still had no detectable WHsAg and DNA polymerase activity, and the two remaining controls were found to have increasing titres of WHsAg and strong DNA polymerase activity. The results of these studies, which appear in Table II, below, demonstrate the effectiveness of *Phyllanthus niruri* L. extracts in inhibiting chronic hepatitis virus infection.

EXAMPLE 3

This example describes the mouse toxicity test of the aqueous extract of *Phyllanthus niruri* L.

(a) Determination of concentration of aqueous extract of *Phyllanthus niruri* L.

Exactly 1 ml. of the aqueous extract was placed in a preweighed vial and the vial was kept in a vacuum chamber containing a desiccant (solid NaOH). After 48 hours, all the water had evaporated off and the vial was weighed accurately. The vial was kept in the vacuum desiccator for another 24 hours and then the vial was weighed again. This process was repeated until the weight of the vial was constant over two consecutive weighings.

| | |
|---|---|
| Tare weight of empty vial = | 6.623 g |
| Weight of vial after drying 1 ml. of the extract in the vial = | 6.641 g |
| Dry weight of the extract (1 ml) | 0.018 g |
| Concentration to the extracts = | 18 mg/ml |

(b) Mouse Toxicity Experiments: Eight sets of mice, each set containing 5 mice each were assembled in box cages. Each of 5 mice were weighed together. Four sets (total of 20 mice) were marked "Test", and were given aqueous extract of *Phyllanthus niruri* L. (0.1 ml 1.8 mg/ml. intraperitoneally. The other four sets (5-8) were marked "Control" and were given phosphate buffered saline, pH 7.2, also intraperiteneally.

After 3 days each group of mice was weighed and the weights were recorded. None of the mice in either the test or the control sets appeared sick, nor did any lose weight.

After seven days, each group of mice was once again weighed. It was noticed that in test group 3, one of the five mice had died. Autopsy did not reveal any liver toxicity. It was concluded that the mouse had died of causes other than due to the extract of *Phyllanthus niruri* L. There was a net gain in the average weight of the mice.

The toxicity test data appears in Table III below.

TABLE II

| | | | *Phyllanthrus niruri* L. extract | | | | Control (PBS) | | |
|---|---|---|---|---|---|---|---|---|---|
| | | | Code No. | | | | | | |
| | | | 319 | 339 | 360 | 376A | 370 | 388 | 117 |
| Date of Treatment | Date of Bleeding | Number of Days | WHsAg titre* | | | | | | |
| | 7-27-84 | −12 | 1024 | 256 | 1024 | 2048 | 1024 | 2048 | — |
| Start 8-9-84 | | 0 | | | | | | | |
| | 8-16-84 | 7 | 512 | 512 | 2048 | 8192 | 1024 | 2048 | — |
| | 8-21-84 | 12 | — | — | — | — | — | — | 1024 |
| | 8-24-84 | 15 | 512 | 512 | 1024 | 1024 | 1024 | 1024 | — |
| | 8-30-84 | 21 | 8 | 80 | 640 | 2048 | 640 | 1024 | 160 |
| | 9-06-84 | 28 | Neg | Neg | 80 | 1280 | 1280 | 640 | — |
| | 9-12-84 | 34 | — | — | — | — | — | — | 640 |
| | 9-14-84 | 36 | Neg | Neg | Neg | 1280 | 1280 | 160 | |
| | 9-20-84 | — | — | — | — | — | 1280 | | |
| | 9-28-84 | 50 | Neg | Neg | Neg | 2560 | — | 160 | 160 |
| | 10-01-84 | — | — | — | — | 2560 | — | — | |
| | 10-04-84 | 56 | Neg | Neg | Neg | — | 1280 | 1280 | 640 |
| | 10-12-84 | 64 | Neg | Neg | Neg | Animal | 640 | 80 | Animal |
| | 10-19-84 | 71 | Neg | Neg | Neg | Died | 1280 | 160 | Died |
| | 10-25-84 | 77 | Neg | Neg | Neg | | 640 | 300 | |
| Stop Treatment | | | | | | | | | |
| | 11-01-84 | 84 | Neg | Neg | Neg | — | 2560 | 640 | |
| | 11-08-84 | 91 | Neg | Neg | Neg | | 2560 | 640 | |
| | 11-15-84 | 98 | Neg | Neg | Neg | | 1280 | 640 | |
| | 11-23-84 | 106 | Neg | Neg | Neg | | 2560 | 2560 | |
| | 11-30-84 | 113 | Neg | Neg | +20 | | 2560 | 1280 | |
| | 12-06-84 | 119 | Neg | Neg | Neg | | 2560 | 1280 | |
| | 12-14-84 | 127 | Neg | Neg | Neg | | 5120 | 2560 | |
| | 12-18-84 | 131 | — | — | — | | 10240 | — | |
| | 12-21-84 | 134 | Neg | Neg | Neg | | — | 5120 | |
| | 12-28-84 | 141 | Neg | Neg | Neg | | — | 1280 | |
| | 1-04-85 | 148 | Neg | Neg | Neg | | — | 2560 | |
| | 1-10-85 | 154 | — | — | — | | 2560 | — | |

*Values expressed as highest dilution which is positive (>0.1 OD)

TABLE III

| Set No. | Total Weight Initial | Average Weight of Each Initial | Total Weight 3rd Day | Average Weight of Each 3rd Day | Total Weight End of 7th Day | Average Weight of Each End of 7th Day |
|---|---|---|---|---|---|---|
| 1[A] | 89.0 g | 17.8 g | 104.2 g | 20.8 g | 122.9 g | 24.6 g |
| 2[A] | 91.5 g | 18.3 g | 101.0 g | 20.2 g | 124.2 g | 24.8 g |
| 3[A] | 88.2 g | 17.6 g | 84.4 (4 mice) | 21.1 | 101.0 (4 mice) | 25.3 g |
| 4[A] | 89.4 g | 17.9 g | 104.8 g | 20.9 g | 125.5 g | 25.1 g |
| 5[B] | 88.5 g | 17.7 g | 112.1 g | 22.4 g | 126.9 g | 25.4 g |
| 6[B] | 88.4 g | 17.6 g | 107.3 g | 21.5 g | 120.2 g | 24.0 g |
| 7[B] | 88.4 g | 17.6 g | 105.1 g | 21.0 g | 121.5 g | 24.3 g |

TABLE III-continued

| Set No. | Total Weight Initial | Average Weight of Each Initial | Total Weight 3rd Day | Average Weight of Each 3rd Day | Total Weight End of 7th Day | Average Weight of Each End of 7th Day |
|---|---|---|---|---|---|---|
| 8[B] | 91.0 g | 18.2 g | 108.3 g | 21.6 g | 126.5 g | 25.2 g |

[A]signifies Test set
[B]signifies Control set

While certain preferred embodiments of the present invention have been described above, it is not intended to limit the invention to such embodiments, but various modifications may be made thereto, without departing from the scope and spirit of the present invention, as set forth in the following claims.

What is claimed is:

1. A composition of matter useful in the treatment of hepatitis B virus infection, which comprises a fraction of *Phyllanthus niruri* L. extract, said fraction containing the methanol extractable components of *Phyllanthus niruri* L., said components having endogenous HBV-DNA polymerase inhibitory activity and HBsAg binding activity.

2. A pharmaceutical preparation for the treatment of hepatitis B virus infection which comprises, as an active ingredient, a fraction of *Phyllanthus niruri* L. extract, said fraction containing the methanol extractable components of *Phyllanthus niruri* L., said components having endogenous HBV-DNA polymerase inhibitory activity and HBsAg binding activity, in an amount effective to inhibit growth of said virus.

3. A pharmaceutical preparation as claimed in claim 2, which includes a biologically acceptable medium.

4. A pharmaceutical preparation as claimed in claim 3, wherein said biologically acceptable medium is a liquid in which the active ingredient is soluble.

5. A pharmaceutical preparation as claimed in claim 4, which contains 18 mg of said active ingredient per ml.

6. A method for treating patients that are carriers of hepatitis B virus infection, as indicated by the presence of HBsAg and hepatitis viral particles in the sera of said patients, said hepatitis viral particles exhibiting endogenous DNA polymerase activity, which comprises administering to said patients a fraction of *Phyllanthus niruri* L. extract, said fraction containing the methanol extractable components of *Phyllanthus niruri* L., said components having endogenous HBV-DNA polymerase inhibitory activity and HBsAg binding activity, in an amount effective to inhibit growth of said virus.

7. A method as claimed in claim 6 wherein said pharmaceutical preparation is administered periodically, until HBsAg and DNA polymerase activity are undetectable by conventional assay.

8. A method as claimed in claim 6 wherein the pharmaceutical preparation is administered in doses containing from about 1 to about 20 mg of said active agent/kg. of body weight.

9. A method as claimed in claim 6, wherein the pharmaceutical preparation is administered parenterally.

10. A method as claimed in claim 9 wherein the pharmaceutical preparation is administered intravenously.

11. A method as claimed in claim 9 wherein the pharmaceutical preparation in administered intraperitoneally.

* * * * *

UNITED STATES PATENT AND TRADEMARK OFFICE
CERTIFICATE OF CORRECTION

PATENT NO. : 4,673,575
DATED : 6/16/87
INVENTOR(S) : P. Venkateswaran, I. Millman, B. Blumberg It is certified that error appears in the above-identified patent and that said Letters Patent is hereby corrected as shown below:

```
In the Title:   "Hepatitus" should be --Hepatitis--.
Column 1,  line 14, "Matrial" should be --Materia--;
           line 61, "viral-releated" should be --viral-
           related--.
Column 3,  line 10, "aueous" should be --aqueous--;
           line 57, "ilustrated" should be --illustrated--.
Column 4,  line 21, "produce" should be --product--.
Column 7,  line 24, delete "6.641 g".
Column 8,  after "the extract in the vial =", toward the end
           of the line, insert --6.641 g--; "Concentration
           to the extracts" should be --Concentration of the
           extract--.
```

Signed and Sealed this

Ninth Day of February, 1988

*Attest:*

DONALD J. QUIGG

*Attesting Officer*   *Commissioner of Patents and Trademarks*